United States Patent [19]

Asano et al.

[11] Patent Number: 4,921,849

[45] Date of Patent: May 1, 1990

[54] INJECTION CONTAINING 3-BENZOYLOXY-1,3,5(10)-ESTRATRIENE-17-[4-{P-(BIS(2-CHLOROETHYL)AMINO)-PHENYL}BUTANOYLOXY)ACETATE AS AN ACTIVE INGREDIENT

[75] Inventors: Kiro Asano, Kukizaki; Satoshi Mitsuhashi, Hino; Kenji Bannai, Toda; Hisayuki Wada, Abiko; Humio Tamura, Kukizaki, all of Japan

[73] Assignee: Kureha Kagaku Kogyo Kabushiki Kaisha, Tokyo, Japan

[21] Appl. No.: 220,596

[22] Filed: Jul. 18, 1988

[30] Foreign Application Priority Data

Jul. 22, 1987 [JP] Japan .................................. 62-182842

[51] Int. Cl.$^5$ ............................................. A61K 31/56
[52] U.S. Cl. .................................................. 514/182
[58] Field of Search ......................................... 514/182

[56] References Cited

U.S. PATENT DOCUMENTS 4,261,910  4/1981  Asano et al. ...................... 260/397.5
4,578,391  3/1986  Kawata et al. ...................... 514/256

*Primary Examiner*—Joseph A. Lipovsky
*Attorney, Agent, or Firm*—Oblon, Spivak, McClelland, Maier & Neustadt

[57] ABSTRACT

Disclosed herein is an injection containing 3-benzoyloxy-1,3,5(10)-estratriene-17-[4-{p-bis(2-chloroethyl)amino)phenyl}butanoyloxy]acetate, which has been known as an orally administrable anti-tumor substance, as an active ingredient and an ester of iodinated poppy oil fatty acid as a solvent.

6 Claims, No Drawings

INJECTION CONTAINING 3-BENZOYLOXY-1,3,5(10)-ESTRATRIENE-17-[4-{P-(BIS(2-CHLOROETHYL)AMINO)PHENYL} BUTANOYLOXY)ACETATE AS AN ACTIVE INGREDIENT

BACKGROUND OF THE INVENTION

The present invention relates to an injection produced by dissolving 3-benzoyloxy-1,3,5(10)-estratriene-17-[4-{p-(bis(2-chloroethyl)amino)phenyl}-butanoyloxy]acetate, as an active ingredient, in an ester of iodinated poppy oil fatty acid.

Hitherto, 3-benzoyloxy-1,3,5(10)-estratriene-17-[4-{p-(bis(2-chloroethyl)-amino)phenyl}butanoyloxy]acetate (hereafter referred to as "the present derivative") has been known as an anti-tumor agent which has an unusual properties of accumulating in cancer cells in a large amount but less accumulating in normal cells, is small in side effect and is strong in anti-tumor effect.

However, although the present derivative is oil-soluble, it does not completely dissolve in ordinary oils, and it has not been able to prepare an injection which can fully exhibit the unusual properties of the present derivative.

So far, the present derivative has exhibited its excellent effects as an orally administrable medicine. The orally administrable anti-tumor agent has advantages than (1) its administration is easy and simple and (2) it can be administered at home and there is no need of visiting hospital or being hospitalized to take the medicine. On the other hand, an oral administration of the present derivative is accompanied with some difficulties, namely, increased dosage of the present derivative is necessary because of its decomposition in a digestive tract and its excretion with feces due too its low adsorption rate in an intestines and further, its anti-tumor effect to some cancers is reduced because it can not reach to the cancers in a sufficient amount due to an inadequate passage in vivo.

Accordingly, the appearance of an injection which can fully exhibit its effect has been strongly wanted.

Meanwhile, esters of iodinated poppy oil fatty acid have been known as an oil for arterial injection, which has a property of accumulating in cancer cells to some extent and an injection of anti-tumor agent, such as adriamycin or mitomycin, using the oil as the solvent has been tested with an expectation of reducing its strong side effects, however, it was impossible to bring the expected effect in reality.

As a result of the present inventors' extensive studies on an injection which can exhibit the specific character of the present derivative, testing various oils as solvents, the present inventors have completed the present invention.

SUMMARY OF THE INVENTION

The object of the present invention is to provide an injection of the present derivative which is known as an orally administrable anti-tumor agent.

Further, the object of the present invention is to provide an injection which can exhibit fully the characteristic features of the present derivative that its anti-tumor effect is large and its side effects are small.

Still further, the object of the present invention is to provide an injection which contains the present derivative as the active ingredient and an ester of iodinated poppy oil fatty acid as the solvent.

DETAILED DESCRIPTION OF THE INVENTION

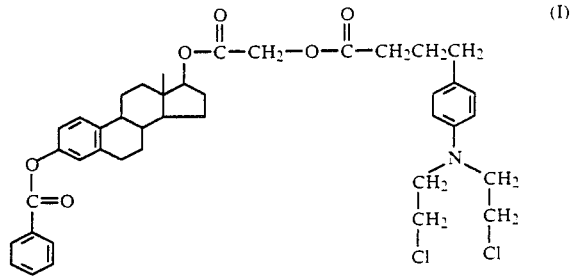

The present derivative is 3-benzoyloxy-1,3,5(10)-estratriene-17-[4-{p-(bis-(2-chloroethyl)amino)phenyl} butanoyloxy]acetate represented by the formula (I) and it can also be named as estra-1,3,5(10)-triene-3,17-diol, 3-benzoate, 17-[4-(bis(2-chloroethyl)amino)phenyl}-1-oxobutoxy]acetate. Further, estradiol which is the skeleton of the present derivative can be estradiol-17β, estradiol-17α or a mixture thereof, however, it is particularly preferable to use the present derivative having estradiol-17β as the skeleton.

The characteristic features of the present derivative as an anti-tumor agent are as follows:

(1) The present derivative is relatively stable in vivo, moves around within a body in a form of benzoate with blood flow or lymph flow and accumulates in larger amount in cancer cells than in normal cells.

However, the present derivative which is benzoate has scarcely any function as an alkylating agent and any affinity to the estradiol-receptor, either.

(2) The present derivative, after entering into cells, is hydrolyzed by an enzyme (the activity thereof is higher in cancer cells) and the benzoic acid group is removed and substituted by a hydroxyl group.

As a result, the present derivative is converted into 3-hydroxy-1,3,5(10)-estratriene-17-[4-{p-(bis(2-chloroethyl)amino)phenyl}butanoyloxy]-acetate (hereinafter referred to as KM-2202). KM-2202 is relatively unstable in cells and has an affinity to the estradiol receptor.

(3) KM-2202 is decomposed slowly into estradiol and chlorambucil within cells and the isolated chlorambucil exhibits its efficacy as an alkylating agent and kills the cells.

As will be understood from the above characteristic features, the present derivative has high anti-tumor effect and small side effects and accordingly, it can be said that the present derivative is one of the so-called anti-tumor agents with high therapeutic effect.

The process for synthesis of the present derivative has been described in detail, for example, in U.S. Pat. No. 4,261,910.

In a mean time, as an ester of iodinated poppy oil fatty acid, a lower alkyl ester of poppy oil fatty acid wherein an iodination degree of 30 to 40% by weight is preferable and the ethyl ester having the iodination degree of 36 to 40% by weight is particularly preferable. For example, LIPIODOL ® (made by Laboratoir Gelbe Co., an ethyl ester of poppy oil fatty acid having iodination degree of 38.8%) can be exemplified.

Concerning an acute toxicity ($LD_{50}$) of the present derivative, even when rats were administered orally with the maximum administrable amount (6,000 mg/kg), no death case has been observed and when rats were injected intraperitoneally in a form of sesame oil solution, its $LD_{50}$ has been over 3,000 mg/kg. Accordingly, the present derivative is a medicine extremely high in safety. In a mean while, $LD_{50}$ of LIPIODOL ® has been 7,000 mg/kg when it was administered intravenously to rabbits.

The present derivative is dissolved in an ester of iodinated poppy oil fatty acid as follows:

0.1 to 10% by weight, preferably 1 to 5% by weight of the present derivative is dissolved into an ester of iodinated poppy oil fatty acid at room temperature to 60° C., preferably 20° to 60° C. for 5 to 30 minutes, preferably 10 to 20 minutes.

As a more preferable method, a supersonic wave or an alcohol can be used to increase a solubility of the present derivative to the ester. As an alcohol, benzyl alcohol can be exemplified and can be added in an amount of 1 to 10% by volume of the ester.

The injection according to the present invention (hereinafter referred to as the present injection) is effective to cancers of digestive tracts such as stomach cancer, colon cancer, esophagus cancer, etc., gynecological cancers such as uterine cancer, ovarian cancer, etc., breast cancer, prostatic cancer, renal cancer, liver cancer, skin cancer, bronchus cancer, lung cancer, thyroid cancer, etc. Especially, it is one of the characteristic features of the present injection that it is effective against cancers such as lung cancer, liver cancer and skin cancer which are relatively unresponsive to an oral administration of the present derivative.

The other characteristic features of the present injection are that the present derivative can be uniformly dissolved in the ester, its administration can easily be performed, that the injection specifically accumulates in a cancer tissue and is distributed even to the peripheral part of the cancer tissues and that the injection is relatively stable in vivo and its anti-cancer effect lasts long. The present injection can work against cancer tissues with a synergistic effect of the present derivative and the solvent.

Moreover, as the present injection is labelled with iodine, it is possible to perform a diagnosis and a medical treatment while observing tumor cells by X-ray, computer tomography, ultrasonic waves, etc. Accordingly, the effective medical treatment can be performed by use of the present injection. Further, the combined application of the present injection with a hyperthermia is also effective.

0.01 to 10 mg/kg of the present derivative in the present injection is preferable as the dosage amount and 0.1 to 5 mg/kg is more preferable.

EXAMPLE 1

A predetermined amount (shown in Table 1) of 3-benzoyloxy-1,3,5(10)-estratriene-17$\beta$-[4-{p-(bis(2-chloroethyl)amino)phenyl}butanoyloxy]acetate or adriamycin was added to 6.5 g of LIPIODOL ® and the mixture was stirred for 15 minutes at 25° C. to obtain a solution as the injection of each active ingredient. Each solution was put into a sterilized vials.

EXAMPLE 2

A walker 256 carcino sarcoma (solid) of about 3 mm square in size was transplanted subcutaneously to the left brachial part and the left femoral part of each of female Wistar rats (the age of 6 weeks and one group consisting of 5 animals) of respective group.

On the 8th or 9th day after the transplantation, each of the injections prepared in Example 1 was injected into each rat of respective testing group from the right femoral artery by a catheter and physiological saline solution or 6.5 g of LIPIODOL ® was injected into each rat of the control group or the LIPIODOL group in the same manner as above.

After having observed the state of the test animals, the mean survival days (MST) and the elongated life time (T/C=test/control) were calculated. The results are shown in Table 1.

TABLE 1

| Exp.No. | Ingredient | MST (day) | T/C (%) |
|---|---|---|---|
| 1 | Control*1 | 17.5 | — |
| 2 | LIPIODOL ® | 18.5 | 105.7 |
| 3 | Present Derivative(100 mg) | 41.0 | 234.3 |
| 4 | Adriamycin(10 mg) | 24.5 | 140.7 |
| 5 | Adriamycin(100 mg) | <1 | <5.7 |

*1 Treated with physiological saline solution.

EXAMPLE 3

Into the liver of each Wistar rat of respective group, Walker 256 carcino sarcoma (solid) was transplanted. Then, each 0.05 ml of the following injection (A), (B) or (C) was injected in the hepatic artery of each rat of each group. On the 7th day of the administration, the blood sample of each rat was collected and the amounts of GOT (glutamic oxaloacetic transaminase) and GPT (Glutamic pyruvic transaminase) were measured.

Further, the liver of each rat was taken out and the concentration of each active ingredient in the hepatic tumor tissue and in the normal hepatic tissue was measured by a high-speed liquid chromatography.

The results are shown in Table 2.

Injection A: A solution prepared by dissolving 10 mg of adriamycin into 0.5 ml of Urografin, further adding 1.5 ml of LIPIODOL ® to the solution and emulsifying the mixed solution by ultrasonic waves.

Injection B: A solution prepared by dissolving 10 mg of 3-benzoyloxy-1,3,5(10)-estratriene-17$\beta$-[4-{p-(bis(2-chloroethyl)amino)phenyl}-butanoyloxy]acetate in 2 ml of LIPIODOL ®.

Injection C: A solution prepared by dissolving 10 mg of 3-benzoyloxy-1,3,5(10)-estratriene-17$\beta$-[4-{p-(bis(2-chloroethyl)amino)phenyl}-butanoyloxy]acetate in 2 ml of sesame oil.

TABLE 2

| Injection | *1 | *2 | GOT (MU/ML) | GPT (MU/ML) |
|---|---|---|---|---|
| A | N.D.*3 | N.D.*3 | 234 ± 45.0 | 31.8 ± 2.1 |
| B | 12.87 ± 5.17 | 4.78 ± 1.98 | 192 ± 76.74 | 52 ± 9.07 |
| C | 7.25 ± 1.69 | 9.83 ± 1.72 | 227 ± 71.12 | 53 ± 5.69 |

*1 Concentration of active ingredient in hepatic tumor tissue ($\mu$g/g wet tissue)
*2 Concentration of active ingredient in hapatic healthy tissue ($\mu$g/g wet tissue)
*3 Not detectable.

What is claimed is:

1. An injectable compositiin prepared by dissolving 0.1 to 10% by weight of 3-benzoyloxy-1,3,5(10)-estratriene-17-[4-{p-(bis(2-chloroethyl)amino)phenyl} butanoyloxy]acetate as an active ingredient in an ester of iodinated poppy oil fatty acid.

2. The injectable composition according to claim 1, wherein said active ingredient is 3-benzoyloxy- 1,3,5(10)-estratiene-17β-[4-{p-(bis(2-chloroethyl)-amino)phenyl}butanoyloxy]acetate.

3. The injectable composition according to claim 1, wherein said ester of iodinated poppy oil fatty acid is an ethyl ester of iodinated poppy oil fatty acid having an iodination degree of 36 to 40%.

4. A method of treating cancer, comprising: injecting a subject to be treated with the injectable composition of claim 1, said subject having a cancer susceptible to said composition.

5. The method according to claim 4, wherein the amount of 3-benzoyloxy-1,3,5-(10)-estratriene-17-[4-{p-bis(2-chloroethyl)amino)phenyl}butanoyloxy]acetate in said composition administered to a subject is 0.05 to 10 mg/kg-body weight.

6. The method according to claim 4, wherein said composition is injected intraarterially.

* * * * *

UNITED STATES PATENT AND TRADEMARK OFFICE
CERTIFICATE OF CORRECTION

PATENT NO. : 4,921,849

DATED : May 1, 1990

INVENTOR(S) : KIRO ASANO ET AL

It is certified that error appears in the above-identified patent and that said Letters Patent is hereby corrected as shown below:

| Col. | Line | |
|------|------|---|
| 1 | 30 | Delete "than" and insert --that--; |
| 4 | 62 | Delete "compositiin" and insert --composition--. |

Signed and Sealed this

Twenty-first Day of April, 1992

Attest:

HARRY F. MANBECK, JR.

Attesting Officer

Commissioner of Patents and Trademarks